United States Patent [19]

Hatfield et al.

[11] Patent Number: 4,683,884
[45] Date of Patent: Aug. 4, 1987

[54] NOISE ATTENUATING SMOKELESS SURGICAL DEVICE

[75] Inventors: Gregory A. Hatfield; Robert E. Lash, both of Foster City, Calif.

[73] Assignee: MD Engineering, Foster City, Calif.

[21] Appl. No.: 850,664

[22] Filed: Apr. 11, 1986

[51] Int. Cl.⁴ .............................................. A61B 17/36
[52] U.S. Cl. .............................. 128/303.14; 128/910; 128/303.17
[58] Field of Search .............. 128/910, 205.12, 201.25, 128/201.29, 205.19, 204.25, 303.14–303.17; 604/35, 319, 320, 321, 905; 433/91, 96; 181/212, 214, 224, 249, 269, 229, 231, 255

[56] References Cited

U.S. PATENT DOCUMENTS

| | | | |
|---|---|---|---|
| 1,611,475 | 12/1926 | Maxim | 181/249 |
| 3,031,760 | 5/1962 | Bender | 433/91 |
| 3,589,363 | 6/1971 | Banko et al. | 604/8 |
| 3,782,497 | 1/1974 | Bidwell et al. | 604/319 |
| 3,906,955 | 9/1975 | Roberts | 128/303.17 |
| 3,990,452 | 11/1976 | Murry et al. | 128/305 |
| 4,192,336 | 3/1980 | Farguhar et al. | 181/214 |
| 4,531,934 | 7/1985 | Kossovsky et al. | 604/35 |

Primary Examiner—Henry J. Recla
Attorney, Agent, or Firm—Harris Zimmerman; Howard Cohen

[57] ABSTRACT

A smokeless, low noise electrosurgical device includes a tubular housing having a passage extending axially therethrough, with one end of the passage connected to a source of negative gauge pressure. The other, inlet end of the housing is provided with an electrosurgical cutting device or cauterizing probe extending therefrom. The inlet to the passage comprises a wide opening having side walls which converge to a relatively narrow port in flow communication with the passage in the housing. The port is significantly narrower than the passage, resulting in significantly reduced noise generated by the fluid flow into the inlet and through the passage.

4 Claims, 3 Drawing Figures

U.S. Patent    Aug. 4, 1987    4,683,884
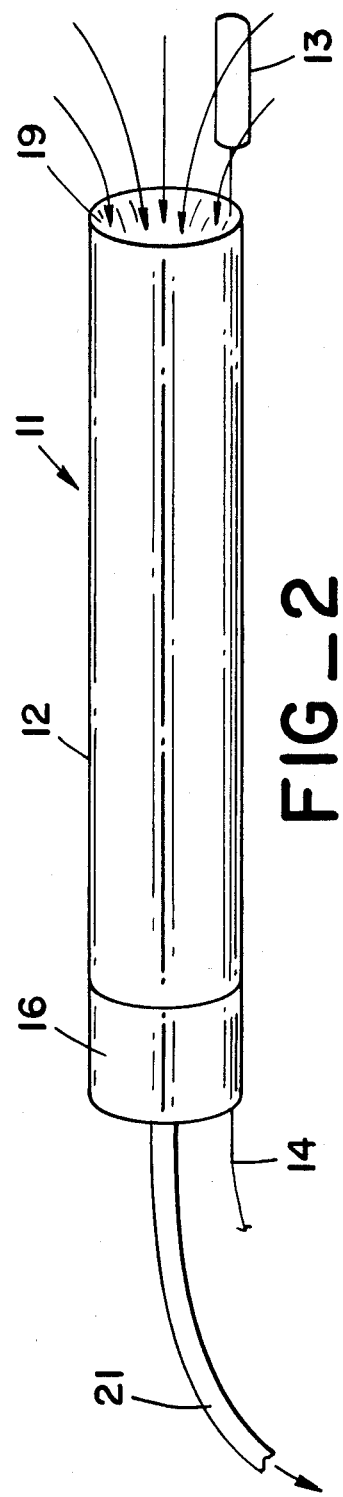
FIG_2
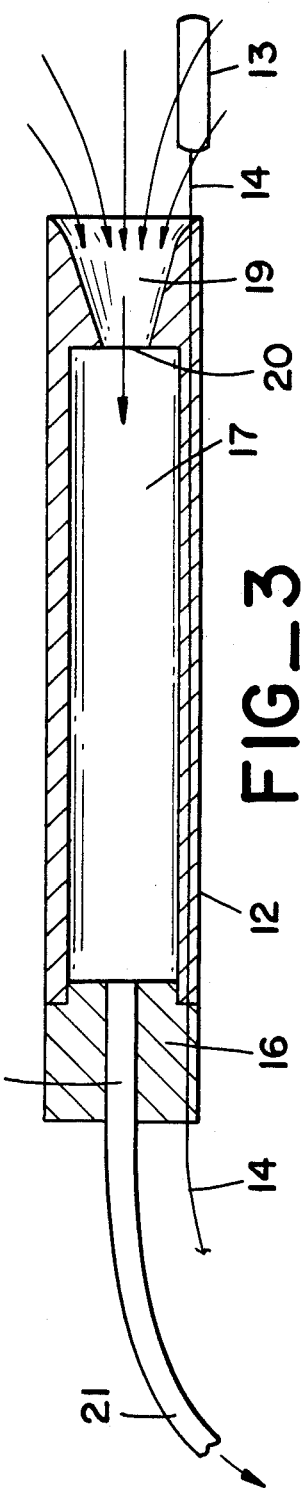
FIG_3
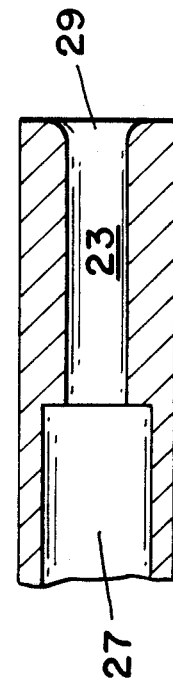
FIG_1 (PRIOR ART)

NOISE ATTENUATING SMOKELESS SURGICAL DEVICE

BACKGROUND OF THE INVENTION

In modern surgical practice it is frequently necessary or desirable to employ electrosurgical tools to effect cutting and simultaneous electrocoagulation of blood and other fluids at the surgical site. A common product of electrocoagulation is smoke and vapor which can obscure the surgical site. Also, the smoke and vapor is generally irritating or noxious to the surgeon and the operting room staff. Thus, prior art tools generally have been provided with suction inlet means directly adjacent to the electrocoagulation member to remove the offensive gases and vapors as they are generated.

These surgical tools are generally relatively small, and the suction inlet is likewise small and narrow. Because of the high fluid flow rate required to remove substantially all of the smoke and vapor which is generated, the suction inlet of a typical prior art device is known to emit a hissing noise which is surprisingly loud. Although this suction noise is not a problem during short term exposure, many surgical procedures are sufficiently time consuming that the hissing noise becomes a significant irritant to the surgeon and others in the immediate area. This noise can also contribute to the fatigue of the surgeon and the operating room personnel.

In recent years the use of laser surgical devices has grown rapidly, and these devices also tend to create large amounts of smoke and vapor. Thus these devices are generally also provided with vacuum induction means adjacent to the laser impact site for immediate removal of the smoke and vapor byproducts. As more of these instruments come into use, it has been noted that the noise radiated by the vacuum induction means is extremely aversive, due to the amplitude and constancy of the noise.

SUMMARY OF THE PRESENT INVENTION

The present invention generally comprises an improved device for removing from a surgical site or the like the noxious smoke and vapor generated as a by-product of procedures such as electrocoagulation, laser surgery, and the like. A salient feature of the invention is the attenuation of the noise created by the fluid flow into the device, resulting in greatly reduced irritation and fatigue to the surgeon or user.

A device includes a tubular housing having a passage extending axially therethrough, with one end of the passage connected to a source of negative gauge pressure. The other, inlet end of the housing is provided with an electrosurgical cutting device, cauterizing probe, or laser output port extending therefrom. The inlet to the passage comprises a wide opening having side walls which converge to a relatively narrow port in flow communication with the passage in the housing. The port is significantly narrower than the passage, so that the fluid flow decelerates as it enters the passage. The noise created by the fluid flow in the passageway, often perceived as hissing or whistling, is reduced by the lowered fluid velocity. Also, the narrow port extending to the inlet blocks the transmission of the noise to the exterior of the device, resulting in significantly reduced noise in the area immediately adjacent to the device.

BRIEF DESCRIPTION OF THE DRAWING

FIG. 1 is a partial cross-sectional view of a typical prior art device for removing smoke and vapor from a site of electrocoagulation or laser ablative surgery or the like.

FIG. 2 is a perspective view of the low noise device of the present invention for removing smoke and vapor from a site of electrocoagulation or laser ablative surgery or the like.

FIG. 3 is a cross-sectional view of the device of the present invention as shown in FIG. 2.

DESCRIPTION OF THE PREFERRED EMBODIMENT

The present invention generally comprises an improved device for removing smoke, vapor and gases from a localized generation site, such as a site of electrocoagulation, laser ablation, or the like. A significant feature of the invention is the reduction in noise compared to similar prior art devices.

In the prior art, it is known to remove such smoke and/or vapor by vacuum induction into a closed channel. For example, with regard to FIG. 1, a typical device includes a tubular member 26 having a bore or passageway 23 extending therethrough, with one end 27 connected to a source of negative gauge pressure. The negative guage pressure in the bore 23 causes the ambient atmosphere to be drawn into the inlet end 29 of the device, the inrushing air carrying with it the offensive smoke, gases, and vapor from the site of generation. The bore 23 is generally linear and formed with a constant diameter or width.

It may be appreciated that the inrushing fluid flow is responsible for generating noise of substantial amplitude. It is theorized that the noise is fluid mechanical in origin; the fluid boundary layer in the bore 23 expands as the flow proceeds through the bore, constricting the channel and increasing the velocity. The higher velocity flow causes the majority of the objectional sound, which is radiated from the opening 29. The flared opening 29 acts as a megaphone to effectively couple the generated noise to the area immediately adjacent to the device.

The present invention generally includes an improved device 11 comprised of a tubular housing 12 having a large diameter bore 17 formed therein. An end plug 16 is secured to the proximal end of the housing 12 in sealing fashion, with an opening 18 extending through the plug and connected to a tube 21. The tube 21 extends to a source of negative gauge pressure. An electrosurgical scalpel or the like extends from the distal end of the housing 12, and is connected to an electrical cable 14. The cable 14 extends through the wall of the housing 12 to the proximal end thereof, and is connected to a suitable electrocoagulation control device. Alternatively, a laser output port may be secured to the distal end of the housing 12, and the cable 14 may be replaced by a fiber optic cable connected to a laser light source.

A significant feature of the invention is the provision of an inlet opening 19 which is only slightly narrower in diameter than the housing itself. THe wall of the inlet opening 19 tapers and narrows to a throat 20 which is substantially smaller in diameter than both the opening 19 and the bore 17. In the preferred embodiment the wall is tapered conically at an angle of 20°–30°, and the throat 20 is approximately one third the diameter of the bore 17.

The negative pressure within the bore causes a vacuum induction of ambient atmosphere into the opening 19, carrying with it the noxious smoke and other airborne vapors, aerosols, gases, and the like. As the inrushing fluid enters the bore 17, the increased width of the flow path causes the fluid flow to decelerate substantially, rather than to accelerate, as in the prior art devices. The reduced fluid velocity lowers the amplitude of the sound generated by the fluid flow through the device. Moreover, the sound generated by the fluid flow in the bore 17 is captured and muffled within the bore by the narrow throat 20, thereby decoupling the sound from the exterior of the device.

Research and testing of the invention have determined that the sound intensity measured directly adjacent to the inlet 19 is approximately 1500 times less than the sound intensity at a similar location relative to the prior art device of FIG. 1. At a proximal position the sound intensity is reduced by a factor of 80. It may be appreciated that these substantial reductions result in significantly reduced irritation and fatigue to the user of the device.

It should be noted that the present invention may be used in conjunction with non-medical devices, such as industrial ablative lasers, soldering stations, and the like.

We claim:

1. In a device for removing smoke and vapor from a generation site by a vacuum induction device, apparatus for reducing acoustic energy generated by the vacuum induction device, including a housing, a bore extending through said housing, means for connecting one end of said bore to a source of negative gauge pressure; intake means at the other end of said bore for receiving ambient atmosphere by vacuum induction, including an intake port disposed at said other end of said bore, said intake port including an outermost opening, a tapered wall extending smoothly inwardly from said intake port to said bore and defining a narrow throat at the inner end thereof, said bore comprising a cylindrical passage having a diameter substantially greater than said throat, said connecting means comprising an end wall at said other end of said bore having a central opening therethrough, said end wall extending generally transverse to the axis of said cylindrical passage, whereby said throat is connected directly to said opening formed centrally in said end wall.

2. The device of claim 1, wherein said tapered wall extends at an angle of approximately 20°–30° with respect to the axis of said bore.

3. The device of claim 2, wherein said tapered wall is formed in the configuration of a frusto-conical section.

4. A smokeless, low noise electrosurgical device, including a tubular housing having a passage extending axially therethrough, one end of said passage adapted to be connected to a source of negative gauge pressure, the other end including a closed, generally transverse end wall, an electrosurgical cutting device connected to and extending from said housing adjacent to the other end of said passage, an inlet adjacent to said electrosurgical cutting device, comprising a wide opening having side walls which converge to a relatively narrow port, said port extending through said end wall, said port being significantly narrower than said passage, resulting in significantly reduced noise generated by the fluid flow into the inlet and through said passage.

* * * * *